United States Patent
Usowicz et al.

(10) Patent No.: US 8,997,587 B2
(45) Date of Patent: Apr. 7, 2015

(54) NEEDLE SEAL FORCE SENSOR

(75) Inventors: James E. Usowicz, Webster, MA (US); Tony A. Lin, Ashland, MA (US); Joshua A. Burnett, Taunton, MA (US); Marc Lemelin, Douglas, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/520,605

(22) PCT Filed: Jan. 10, 2011

(86) PCT No.: PCT/US2011/020626
§ 371 (c)(1),
(2), (4) Date: Oct. 1, 2012

(87) PCT Pub. No.: WO2011/085284
PCT Pub. Date: Jul. 14, 2011

(65) Prior Publication Data
US 2013/0008237 A1  Jan. 10, 2013

Related U.S. Application Data (60) Provisional application No. 61/293,889, filed on Jan. 11, 2010.

(51) Int. Cl.
*G01L 5/00* (2006.01)
*G01N 30/16* (2006.01)
(Continued)

(52) U.S. Cl.
CPC ............ *G01N 30/16* (2013.01); *G01N 35/1011* (2013.01); *G01N 2030/185* (2013.01); *G01L 1/00* (2013.01); *G01N 30/24* (2013.01)

(58) Field of Classification Search
CPC ......... G01N 30/00; G01N 7/00; G01N 30/02; G01N 30/16; G01N 35/10
USPC .......... 73/162.01, 19.02, 818, 422, 42, 61.52, 73/19.05, 19.1, 64.21, 864.23, 864.25; 422/70, 509
See application file for complete search history.

(56) References Cited

U.S. PATENT DOCUMENTS 4,117,727 A * 10/1978 Friswell et al. .............. 73/19.02
4,153,076 A   5/1979 McNeil et al.
(Continued)

FOREIGN PATENT DOCUMENTS

WO   WO 2009/092345 A1   7/2009

OTHER PUBLICATIONS

Snyder, et al., "Introduction to Modern Liquid Chromotography," Second Edition, John Wiley and Sons, Inc., 1979, 43 pps.
(Continued)

*Primary Examiner* — Julio J Maldonado
*Assistant Examiner* — Sheikh Maruf
(74) *Attorney, Agent, or Firm* — Muirhead and Saturnelli, LLC (57) ABSTRACT

Described are techniques for force sensing. A computing device is configured to have a desired force setting. A first vertical position of a needle is determined using the computer device. A control signal is sent from the computing device to a positioning device. In response to the control signal, the needle is positioned at the first vertical position. When in the first vertical position, surfaces of a tip of the needle are in contact with surfaces of an opening of a sealing member and positioning the needle causes application of a force at surfaces of the opening in contact with surfaces of the tip of the needle. In response to application of the force, a spring is compressed a distance that is proportional to the force. The force is measured using a force sensor.

29 Claims, 6 Drawing Sheets

(51) Int. Cl.
*G01N 35/10* (2006.01)
*G01N 30/18* (2006.01)
*G01L 1/00* (2006.01)
*G01N 30/24* (2006.01)

(56) References Cited

U.S. PATENT DOCUMENTS

| | | | |
|---|---|---|---|
| 4,650,588 A | | 3/1987 | Diebold |
| 4,713,974 A | * | 12/1987 | Stone ................ 73/864.23 |
| 5,190,224 A | * | 3/1993 | Hamilton ................ 239/600 |
| 5,194,226 A | | 3/1993 | Tomoff et al. |
| 5,808,203 A | * | 9/1998 | Nolan et al. .................. 73/700 |
| 7,770,465 B2 | * | 8/2010 | Lapstun et al. ............... 73/818 |
| 2009/0223300 A1 | * | 9/2009 | Lapstun et al. ............... 73/818 |
| 2010/0288025 A1 | * | 11/2010 | Hochgraeber ............. 73/61.55 |

OTHER PUBLICATIONS

European Patent Office Search Report dated Sep. 18, 2014.

\* cited by examiner

FIG. 3A $F_R = F_P + F_S + SF$ $F_R$: FORCE REQUIRED
$F_P$: FORCE EXERTED BY PRESSURE
$F_S$: FORCE TO CREATE LOCAL STRESS
SF: SAFETY FACTOR FOR SURFACE IMPERFECTIONS, ETC.

NEEDLE SEAL FORCE SENSOR

RELATED APPLICATION

This application is a National Stage of International Application No. PCT/US2011/20626, filed Jan. 10, 2011, which claims priority to U.S. Provisional Application No. 61/293,889, filed Jan. 11, 2010, which are hereby incorporated by reference

BACKGROUND

1. Technical Field

This application generally relates to measuring force, and more particularly to techniques used to measure force applied in connection with forming a seal.

2. Description of Related Art

Samples may be processed in a laboratory or other environment for a variety of different purposes and applications. Chromatography refers to techniques for separating sample mixtures. Common chromatographic techniques include gas chromatography (GC) and liquid chromatography (LC). With an instrument that performs LC, a liquid sample to be analyzed is introduced in small volumes for analysis. The sample may be injected into a solvent stream which is carried through a column. The compounds in the sample can then be separated by traveling at different speeds through the column resulting in the different compounds eluting from the column at different times. In connection with High Performance Liquid Chromatography (HPLC) and Ultra Performance Liquid Chromatography (UPLC), pressure is used to facilitate fluid flow in the system through the chromatographic column.

In a system that performs LC, a sample may be injected into the system using different techniques. One technique is fixed loop injection where a sample may be aspirated into a needle, positioned in a sample loop, and then carried through to the column. With fixed loop injection, the sample loop becomes part of the fluid path. Another technique is direct injection where a sample is aspirated into a needle and the sample is directly injected into the system so that the needle becomes part of the fluid path. With direct injection, after the sample is aspirated into a needle, the needle may be positioned at a surface of a sealing member. The needle has sufficient force applied thereto so that the needle tip forms a seal at the surface of the sealing member when the LC system is subsequently pressurized. The sample in the needle is then carried through to the column, such as by a solvent. In direct injection such as may be used in UPLC or HPLC systems, the sealing member is subjected to conditions that affect its useful lifetime. A component or part, such as a sealing member, having a surface used in forming a seal may be replaced, for example, when an adequate seal cannot be formed and/or maintained resulting in sample leakage. In such a case, the component or part may be characterized as having reached the end of its useful lifetime. The conditions under which the components, and surfaces thereof where seals are formed, operate may affect the lifetime, or amount of time, the component may be used in an LC or other system prior to replacement. Such conditions include the pressure applied in forming the seal between the surfaces at the needle tip and sealing member. If excessive force is applied in the foregoing, the sealing member may be subjected to additional wear further reducing its useful lifetime.

SUMMARY OF THE INVENTION

In accordance with one aspect of the invention is an apparatus comprising a needle positioned at a vertical position; a positioning device configured to position the needle at the vertical position in response to control signals; a sealing member having a passage with a first opening at a first end for receiving one end of the needle, wherein positioning the needle at the vertical position causes application of a force at surfaces of the sealing member in contact with surfaces of said one end of the needle; a spring which, responsive to application of the force, is compressed a distance proportional to the force; a force sensor coupled to the spring, the force sensor measuring the force; and a computing device electrically connected to the force sensor and the positioning device. The computing device is configured to receive a signal from said force sensor indicating said force measured by the force sensor. The computing device may be further configured to determine an adjustment to the vertical position of said needle in accordance with whether said force measured by said force sensor is at a desired force setting, and configured to send control signals to said positioning device causing said positioning device to vertically position said needle in accordance with said adjustment. The computing device may include a computer processor. The apparatus may also include a computer readable medium comprising executable code stored thereon that: determines an adjustment to the vertical position of the needle in accordance with whether the force being applied is at the desired force setting; and sends control signals to the positioning device causing the positioning device to vertically position the needle in accordance with an adjustment determined by the code that determines an adjustment. The positioning device may include a motor which incrementally adjusts vertical positioning of the needle responsive to control signals from the computing device. The desired force setting may be an amount of force determined as sufficient to create a seal at the surfaces of the sealing member which are in contact with said one end of the needle when a system including the apparatus is pressurized. The apparatus may be included in a system that performs liquid chromatography. The apparatus may be included in a component that performs direct injection of a sample aspirated into the needle. The sealing member may be a needle seal and the first opening at said first end thereof may be inwardly tapered and sidewalls of said first opening may be in contact with a tip at said one end of the needle. The computer readable memory may further include executable code stored thereon that compares said force measured by said force sensor to said desired force setting to determine whether to make any adjustment to said vertical position of said needle. The computer readable memory may further include executable code stored thereon that: determines, if the force measured is less than the desired force setting, an adjustment which, when applied to the needle, causes the needle to be further adjusted vertically downward causing the spring to compress another amount in addition to the distance. The computer readable memory may further include executable code stored thereon that determines, if the force measured is more than the desired force setting, an adjustment which, when applied to the needle, causes the needle to be further adjusted vertically upward causing the spring to compress a lesser amount than the distance. The desired force setting may vary in accordance with an operating pressure of a system including the apparatus. The force sensor may include a load cell.

In accordance with another aspect of the invention is a method for force sensing. A computing device is configured to have a desired force setting. Using the computing device, determining a first vertical position of a needle. A control signal is sent from the computing device to a positioning device. In response to the control signal, the needle is positioned using the positioning device at the first vertical position. When in the first vertical position, surfaces of a tip of said needle are in contact with surfaces of an opening of a sealing member and said positioning causes application of a force at surfaces of the opening in contact with surfaces of the tip of the needle. Responsive to application of the force, a spring is compressed a distance that is proportional to the force. The force is measured using a force sensor. The method may also include determining, using the computing device, whether to adjust the first vertical position of the needle in accordance with whether the force measured using the force sensor is at a desired force setting. The computing device may include a computer processor which executes code to perform processing, said processing including said determining a first vertical position, said sending, and said determining whether to adjust the first vertical position. The method may include receiving, by the computing device, a signal from the force sensor, the signal indicating the force measured by the force sensor; comparing, using the computing device, the force measured by the force sensor to the desired force setting; and determining, using the computing device, a vertical positioning adjustment in accordance with said comparing. If the measured force is less than the desired force setting, the method may further include determining a vertical positioning adjustment which, when applied to the needle, causes the first vertical position of the needle to be further adjusted vertically downward causing the spring to compress another amount in addition to the distance If the force measured is more than the desired force setting, the method may further include determining, a vertical positioning adjustment which, when applied to the needle, causes the first vertical position of the needle to be further adjusted vertically upward causing the spring to compress a lesser amount than the distance. If the measured force is less than the desired force setting, the method may further include determining a vertical positioning adjustment wherein the first vertical position of the needle is further adjusted vertically downward causing the spring to compress another amount in addition to the distance. If the force measured is more than the desired force setting, the method may also include determining a vertical positioning adjustment wherein the first vertical position of the needle is further adjusted vertically upward causing the spring to compress a lesser amount than the distance. The desired force setting may be an amount of force determined as sufficient to create a seal at the surfaces of the sealing member which are in contact with surfaces of the tip of the needle when a system in which the method is being performed is pressurized. The force may be a sealing force applied in a system that performs liquid chromatography. Vertical positioning of the needle may be readjusted until the measured force equals the desired force setting determined as sufficient to form a seal at the surfaces of the sealing member which are in contact with surfaces of the tip of the needle when a system in which the method is being performed is pressurized. The method may also include aspirating a sample into the needle prior to positioning the needle at the first vertical position. The desired force setting may vary in accordance with an operating pressure of a system in which the method is performed. The force sensor may include a load cell. The sealing member may be a needle seal. The method may also include determining that the sealing member should be replaced if the force measured by the force sensor is at least the desired force setting and a seal is not formed at surfaces of the tip in contact with surfaces of the opening of the sealing member when a system is pressurized. The method may also include determining a problem if a maximum downward vertical position of the needle does not cause a force measured by the force sensor to be at least equal to the desired force setting.

BRIEF DESCRIPTION OF THE DRAWINGS

Features and advantages of the present invention will become more apparent from the following detailed description of exemplary embodiments thereof taken in conjunction with the accompanying drawings in which.

DETAILED DESCRIPTION OF
EMBODIMENT(S)

Described in following paragraphs are techniques that may be used in measuring force applied in connection with forming a seal. The force applied is one of the conditions affecting the lifetime of components, such as sealing members, having a surface thereof at which the seal is formed. Techniques described in following paragraphs may be used in connection with an embodiment such as a liquid chromatography (LC) system. The LC system may be, for example, a High Performance Liquid Chromatography (HPLC) or an Ultra Performance Liquid Chromatography (UPLC) system such as the ACQUITY UPLC® and nanoACQUITY UPLC® systems from Waters Corporation of Milford Mass. An LC system such as the foregoing from Waters Corporation may operate under high pressure such as in the range of 5,000 pounds per square inch or psi (e.g., exemplary for some HPLC systems) to 15,000-20,000 psi (exemplary for some UPLC systems). The foregoing exemplary pressures should not be construed as a limitation. The techniques herein may be used in an embodiment of an LC or other system which operates at pressures different from, and/or higher than, the foregoing exemplary pressures. An LC system may include an injector used to inject controlled volumes of a sample, either manually or automatically, into a fluid stream which carries the sample to an LC column where the sample may then be separated. As described in following paragraphs and figures, an exemplary embodiment in accordance with techniques described herein may be a UPLC or HPLC system using direct injection to introduce a sample for analysis. In a direct injection LC system, a sample may be aspirated into a needle and the needle becomes part of the system flow path. For example, the Alliance HPLC® System by Waters Corporation uses direct injection.

As known in the art, an LC system using direct injection may aspirate a sample into a needle and position the needle at a surface of a sealing member. The needle may have a sufficient force applied thereto so that the needle tip forms a seal at the surface of the sealing member when the LC system is subsequently pressurized. The sample in the needle is then carried through to the column, such as by a solvent. The techniques described in following paragraphs provide for force sensing to measure the force applied to the needle in forming the foregoing seal between the needle tip and sealing member.

The seal formed between the needle tip and surface of the sealing member may be characterized as a dynamic seal. A dynamic seal may be defined as a seal where there is relative movement between the surfaces forming the seal. In contrast to a dynamic seal is a static seal where there is no relative movement between surfaces forming the seal. It should be noted that the term sealing member may be used to generally refer to a part such as a needle seal which may be used in forming a dynamic seal. In connection with dynamic seals, the surfaces in contact with one another experience wearing affecting the lifetime of the components used in forming the seal. In connection with direct injection, surfaces of the needle seal in contact with the needle tip are subject to wear. The amount of force applied at the foregoing surfaces in forming the seal is one condition that affects the lifetime of the needle seal. In various systems such as UPLC and HPLC systems operating under high system pressures, high sealing pressures are required thereby further reducing the lifetime of the needle seal than when using lower sealing pressures.

As described in following paragraphs and figures, an embodiment using the force sensing techniques described herein provides advantages of using lower sealing forces that do not have to account for worst case conditions as related to mechanical tolerances, positional tolerances, and the like. Such worst case conditions are considered when selecting a force for use in a system which does not utilize the force sensing techniques herein thereby resulting in higher sealing forces in comparison to embodiments using the force sensing techniques herein. The force sensing techniques herein provide for automatic adjustments to vertical needle positioning when the required sealing force changes such as due to a change in operating system pressure. Such automatic adjustments provide an advantage of not requiring, for example, a service call for manual system recalibration to change the sealing force applied. The foregoing, as well as other uses and advantages of the techniques herein, will be appreciated by those of ordinary skill in the art in light of the description set forth in following paragraphs.

Figure 1:
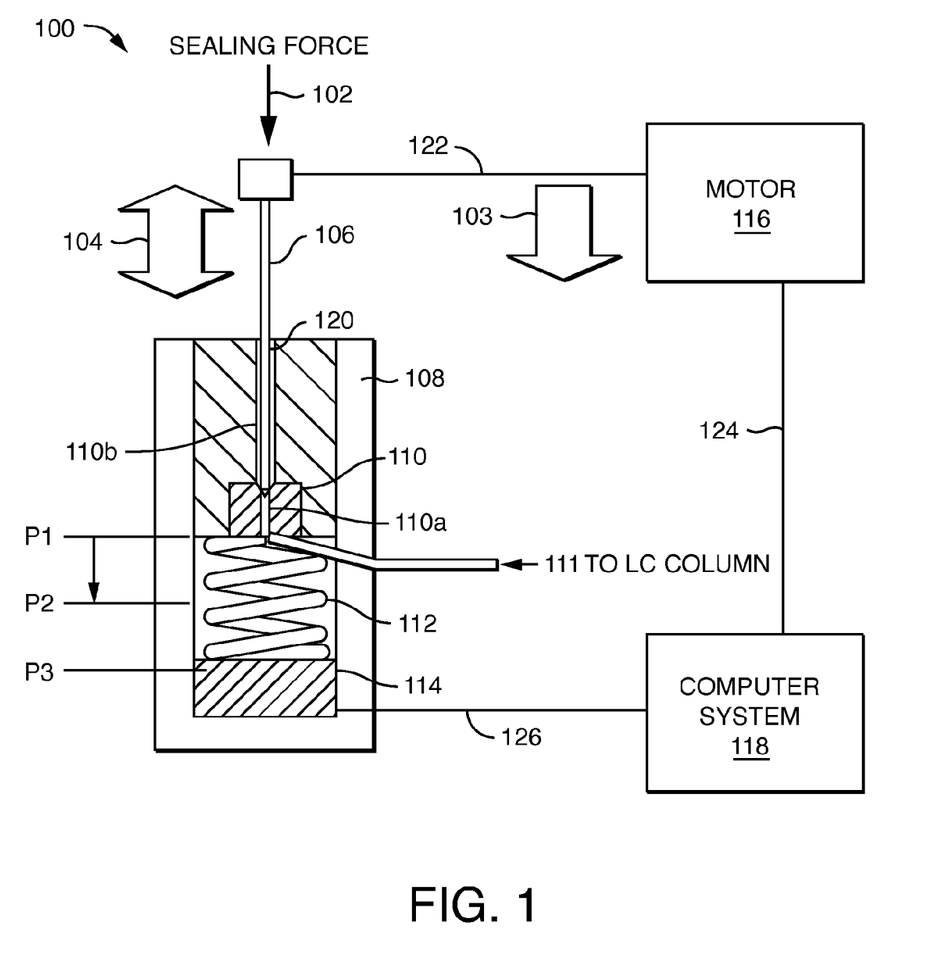
FIG. 1 is an example illustrating components that may be included in an embodiment in accordance with techniques described herein.

Referring to FIG. 1, shown is an example of components that may be included in an embodiment of an LC system in accordance with techniques described herein. The example 100 illustrates components that may be included in a sample manager of the LC system which uses direct injection to introduce controlled amounts of a sample into the LC system. The example 100 illustrates a sealing force 102, needle 106, housing 108, needle seal 110, spring 112, load cell 114, motor 116, and computer system 118.

The needle seal 110 may be formed using one any suitable material such as, for example, a polymeric material, steel, and the like, using any suitable manufacturing technique, such as machining. An example of a needle seal 110 and needle 106 that may be used in an embodiment including the components of FIG. 1 are described in U.S. Provisional Patent Application No. 61/293,879, filed on Jan. 11, 2010, STATIC AND DYNAMIC SEALS, ("STATIC AND DYNAMIC SEALS application"), which is incorporated by reference herein.

The needle seal 110 may be characterized as forming a dynamic seal during operation of a direct injection technique to introduce a sample into the LC system. In connection with performing direct injection, a sample may be aspirated into the needle 106. At a first point in time, the needle 106 is then inserted into opening 120 with a sufficient downward force (e.g., sealing force 102) in the vertical direction. The needle 106 is positioned into opening 110a in the needle seal 110 so that the needle tip of needle 106 comes into contact with sidewalls within the opening 110a in the needle seal 110 to form a seal when such sufficient force is applied. An enlarged view of a portion of an embodiment of the needle seal is illustrated in following figures and also in the STATIC AND DYNAMIC SEALS application. The passage 110b having opening 120 may be formed to have a shape and sufficient size to accommodate the needle 106 and allowing the needle 106 to come into contact with the sidewalls of 110a as just described. As illustrated in FIG. 1, the opening 110a is at one end of a throughhole through the needle seal 110. The inner sidewalls of 110a at the end where the needle is introduced are tapered and narrowed to a point so that the needle tip, when inserted into 110a, comes into contact with the inner sidewalls of 110a as it narrows. It is at the foregoing points of contact between the needle tip and inner sidewalls of 110a that the seal is formed. As described above, the needle is inserted with a sufficient amount of force necessary to form the seal between surfaces of the needle tip and needle seal so that when the system is pressurized, the sample, such as a fluid, does not leak from the foregoing surfaces.

As described above, the needle 106 is inserted into 120, through 110b, and the needle tip comes into contact with the sidewalls of 110a. Once in contact with the sidewalls of 110a, further downward vertical movement of the needle 106 results in the needle seal also being pushed downward so as to compress the spring 112 toward the load cell 114. As an example, the foregoing downward force applied to the needle may cause the needle seal 110 to advance in a downward vertical direction from P1 to P2 thereby causing compression of the spring 112 by the distance or length of P2-P1. The load cell 114 may measure the force exerted upon it due to the compression of spring 112. The force measured by the load cell is equal to the force exerted at the surface areas of contact between the needle tip and the needle seal 110. The needle seal 110 may be allowed sufficient vertical movement within the housing 108 so that the spring 112 is compressed by the force 102 applied to the needle 106 during this insertion. When the applied force 102 is removed (e.g., such as when the needle is pulled upward removing the needle from 120, the spring 112 and the needle seal 110 return the original or starting positions denoted by P1.

As known in the art, the load cell 114 may be characterized as an electronic device used to convert a force exerted thereon into an electrical signal which may be communicated over connection 126 to the computer system 118. Connection 126 may be an electrical connection facilitating communication of the output signal from the load cell 114 to the computer system 118. The computer system 118 may be executing code thereon which processes the signals received over 126. The signal output by the load cell 114 may indicate the amount of force exerted on the load cell 114 by the spring 112. The computer system 118 may be programmed to compare the force measured by 114 (as communicated by the signal from 114 to 118 over 126) with a desired force. The computer system 118 may determine whether the needle 106 needs to be moved further downward in the vertical direction 103 within 110b depending on differences between the measured force and the desired force. If the computer system 118 determines that additional force needs to be applied to the needle 106 to achieve the desired force, the computer system 118 may issue control signals to the motor 116 over electrical connection 124 causing the motor 116 to move the arm 122 and needle 106 further downward in the vertical direction 103. The additional vertical distance that needle 106 is moved downward causes additional force to be exerted by the needle tip on the needle seal 110, further causing additional compression of spring 112. The computer system 118 may continue to receive measured force readings from the load cell 114 and accordingly make any appropriate adjustments to the vertical positioning of the needle 106 in order to achieve the desired force. Adjustments to the vertical positioning of the needle 106 within 110b may be performed in an incremental manner. For example, the needle 106 may be positioned at a first vertical distance within 110b where the needle tip contacts and exerts a first force on the needle seal 110 causing compression of spring 112. A first force measurement may be obtained by the load cell 114 and communicated to the computer system 118. In response to determining that the first force measurement is less than a desired amount of force, the computer system 118 may instruct the motor 116 to move arm 122 an additional vertical distance in the direction 103 causing further compression of spring 112. The components of FIG. 1 may provide for repeatedly performing the foregoing steps of determining a force measurement by the load cell and having the computer system issue commands to the motor making further adjustments to the vertical needle position until the computer system 118 determines that the measured force communicated by the load cell 114 is equal to a desired force (within acceptable force threshold limits). Each such adjustment may result in positioning the needle 106 an additional vertical distance in direction 103 within 110b. The ending vertical position of the needle 106 (when the computer system 118 determines that the desired force is being exerted) may vary with aspects of each system such as, for example, the operating pressure of the LC system (e.g., 5,000 psi or 20,000 psi). As illustrated by 104, the arm 122 may be moved upward or downward to various vertical positions using motor 116. In a manner similar to that as described above when measured force is less than a desired force, the arm 122 may be adjusted in an upward vertical direction when the measured force exceeds the desired force.

The load cell 114 may be, for example, a commercially available load cell such as strain gauge load cell from Measurement Specialties, Part No. ELAF-E2204-0010L, Description ELAF-B0-10L/L01F/M33P/Z2 or Description ELAF-B0-10L/L01F/M50P/Z2. The motor 116 may be stepping motor which causes adjustment to the vertical positioning of the arm 122 in fixed or predetermined increments. The motor 116 may be, for example, a stepper motor by Sanyo-Denki (P/N 103H5212-4541) or Vexta (P/N C9257-9012P-C1)

The spring 112 may be made of stainless steel having a spring rate of 65.7 lbs/inch, and outer diameter of 0.360 inches and a wire diameter of 0.047 inches. The distance between P1 and P3 representing the spring in its natural or uncompressed state may be 0.500 inches.

The computer system 118 may be any commercially available or proprietary computer system, processor board, ASIC (application specific integrated circuit), or other component which includes a computer processor configured to execute code stored on a computer readable medium. The processor, when executing the code, may cause the computer system 118 to perform processing steps as described in accordance with techniques herein. As will be appreciated by those skilled in the art, the code may be stored on any type of computer-readable medium having any one of a variety of different forms including volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired code which can accessed by a computer processor. The computer system, processor board, and the like, may be more generally referred to as a computing device. The computing device may also include, or otherwise be configured to access, a computer readable medium comprising executable code stored thereon which cause a computer processor to perform processing steps as described in accordance with techniques herein.

Once the needle is inserted into the needle seal 110 as just described and an appropriate desired amount of force is present at the contacting surfaces of the needle tip and needle seal sidewall surfaces within the opening 110a, the system is pressurized to its operating pressure (e.g., 15,000 psi for an HPLC system) and fluid flow is turned on (e.g., the sample is injected). The sample is carried through a fluid path formed of the needle, through the needle seal 110 and out through port and associated connection 111 to the LC column. It should be noted that connection 111 may be any type of fluid connection or conduit such as a tubing made of metal or other suitable material. The fluid flow through the needle is then stopped while the system is still pressurized. The needle 106 is then pulled in the upward vertical direction out of the needle seal 110 so that a seal is no longer formed where the surfaces of the needle tip contact the inner sidewalls of 110a thereby causing depressurization.

It should be noted that the motor 116 and arm 122 may be more generally referred to as a components comprising a positioning device to position the needle 106 to a desired vertical position in accordance with techniques described herein. The load cell 114 may also more generally be referred to as a force sensing device or force sensor. An embodiment in accordance with techniques herein may use other components than as provided herein for purposes of example and illustration. For example, an embodiment in accordance with techniques herein may use any one or more suitable components as the force sensing device or force sensor, and any one or more suitable components as the positioning device.

Figures 2, 2A:
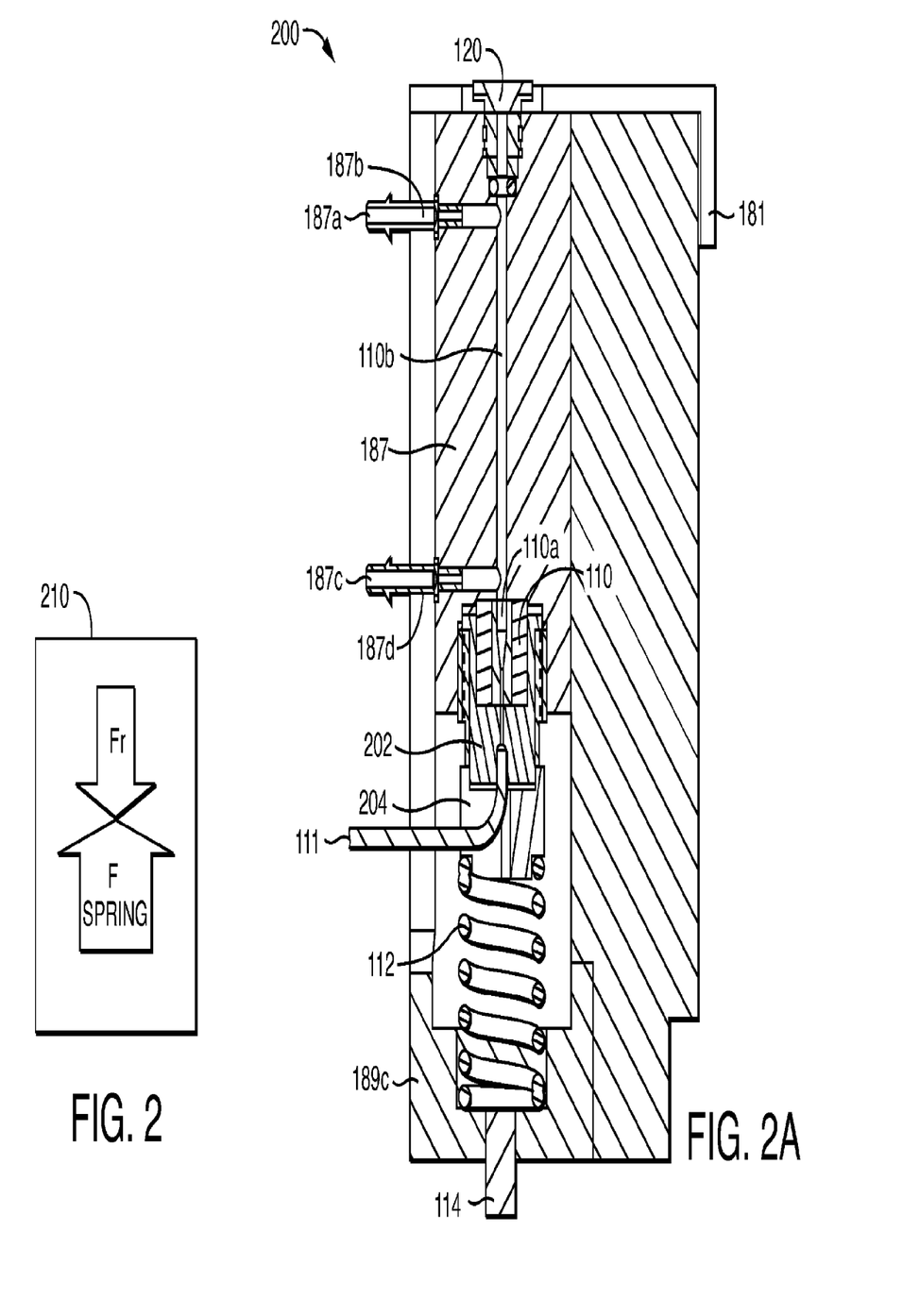
FIG. 2 is an example illustrating additional detail of some of the components of FIG. 1 as may be used in an embodiment in accordance with techniques described herein.

Referring to FIG. 2, shown is an example illustrating additional detail of some components from FIG. 1 as may be included in an embodiment in accordance with techniques herein. The example 200 includes features as described in connection with FIG. 1 such as those denoted by the same element numbers used in FIG. 1. Additionally, the example 200 further illustrates an embodiment where the needle seal 110 may be positioned within component 202 which is in contact with spacer 204. The spacer 204 may provide for additional spring support. Application of downward vertical force to the needle inserted into 120 and 110b causes the needle tip to contact the surface of the needle seal 110 within 110a forming a seal. The force applied causes the needle seal 110, along with components 202 and 204, to move in the downward vertical direction thereby compressing spring 112. The distance of the downward vertical movement (e.g., as illustrated by P1 and P2 of FIG. 1), and thus the amount of compression of spring 112, is proportional to the force being applied.

As known in the art, the foregoing force as related to the amount of spring compression may be characterized by the following equation based on Hooke's law:

$$F = -k*x \quad \text{EQUATION 1}$$

where x is the displacement vector or distance and direction in which the spring is deformed (e.g., such as represented by P2-P1 in FIG. 1);

F is the resulting force vector or magnitude and direction of the restoring force the spring exerts; and k is a spring or force constant of the spring.

Thus, based on the foregoing, the force with which the spring pushes back (Fspring) is linearly proportional to the distance x that the spring is compressed with respect to its equilibrium length (e.g., such as illustrated by P1 of FIG. 1). Additionally, Fspring is equal to the force exerted and applied in forming the seal at the surfaces of the needle tip and needle seal. The vertical positioning of the needle may be varied causing the spring compression or displacement x, and Fspring, to also accordingly vary. The vertical position of the needle may be selected in accordance with an amount of desired or required force, Fr, sufficient to form the seal when the system is pressurized. Element 210 illustrates that the foregoing Fspring, or reactive spring force, is equal to Fr, the amount of force applied to the needle and thus at the contacting surfaces of the needle tip and needle seal. The distance x by which the spring compresses is directly proportional to a vertical distance or positioning of the needle (e.g., If the needle is positioned vertically downward relative to its current position, spring compression and applied force increases. If the needle is positioned vertically upward relative to its current position, spring compression and applied force decreases.)

Also illustrated are ports 187a, 187b through which different solvents or other fluids may flow into/out of such as for washing the needle inserted into 110b. As described in more detail in U.S. Provisional Patent Application No. 61/293,902, filed Jan. 11, 2010, INJECTION PORT NEEDLE SUPPORT AND WASHING, which is incorporated by reference herein (the "NEEDLE SUPPORT AND WASHING patent application"), the material denoted by 187, the passageway 110b formed therein, and optionally ports 187a, 187c and their respective connections 187b, 187d to 110b may comprise a needle support structure. Passageway 110b may have a diameter, for example, within the range of 0.062+/−0.003 inches for use to accommodate the range and dimensions of needles that may be used. It should be noted that the needle support structure may have suitable dimensions to accommodate desired needle diameters and/or lengths that may be used in an embodiment. Element 110b refers to a passageway or conduit into which the needle is inserted and may be surrounded by a material 187 such as stainless steel or one of a variety of different suitable PEEK (polyether-ether-ketone) materials known in the art. As described above, element 202 may be a component holding the seal. Element 204 may be a spacer. Element 189c may be a spring support or cup.

It should be noted that the components of an injection port as of FIG. 2 may be included within a housing. The components illustrated in FIG. 2 may be made of any suitable material and manufactured using any suitable means and techniques known in the art. For example, the needle support structure material 187 as well as the connections 187b, 187d connecting ports 187a and 187c to 110b may be made of a PEEK material. The housing may be made of aluminum. The spring 112, tubing used in connection with 111, and components 202, 204 and 189c may be made from stainless steel.

As illustrated in connection with FIG. 2, needle seal surfaces are in contact with the passageway 110b and there is a substantially fluid tight connection therebetween. Similarly, there may be substantially fluid tight connections between connections 187b and 110b, and between 187d and 110b included in the path of the washing fluid for needle washing. As will be appreciated by those skilled in the art, although not explicitly stated, connections between other components illustrated and described in FIG. 2 and others herein may also be characterized as fluid tight so as not to allow undesirable leakage of the sample, washing fluid, and the like.

The components of FIG. 1 and FIG. 2 may be characterized as providing a feedback loop regarding the force applied to the needle in obtaining the seal where the feedback loop provides for adjusting the vertical positioning of the needle, and thus the amount of spring compression, to obtain a desired or required force Fr.

The amount of desired or required force Fr which is applied in connection with the needle seal and inserted needle may be determined using any of a variety of techniques known in the art. Following paragraphs and figures illustrate how a required force Fr may be determined in an embodiment in accordance with techniques described herein.

Figures 3, 3A:
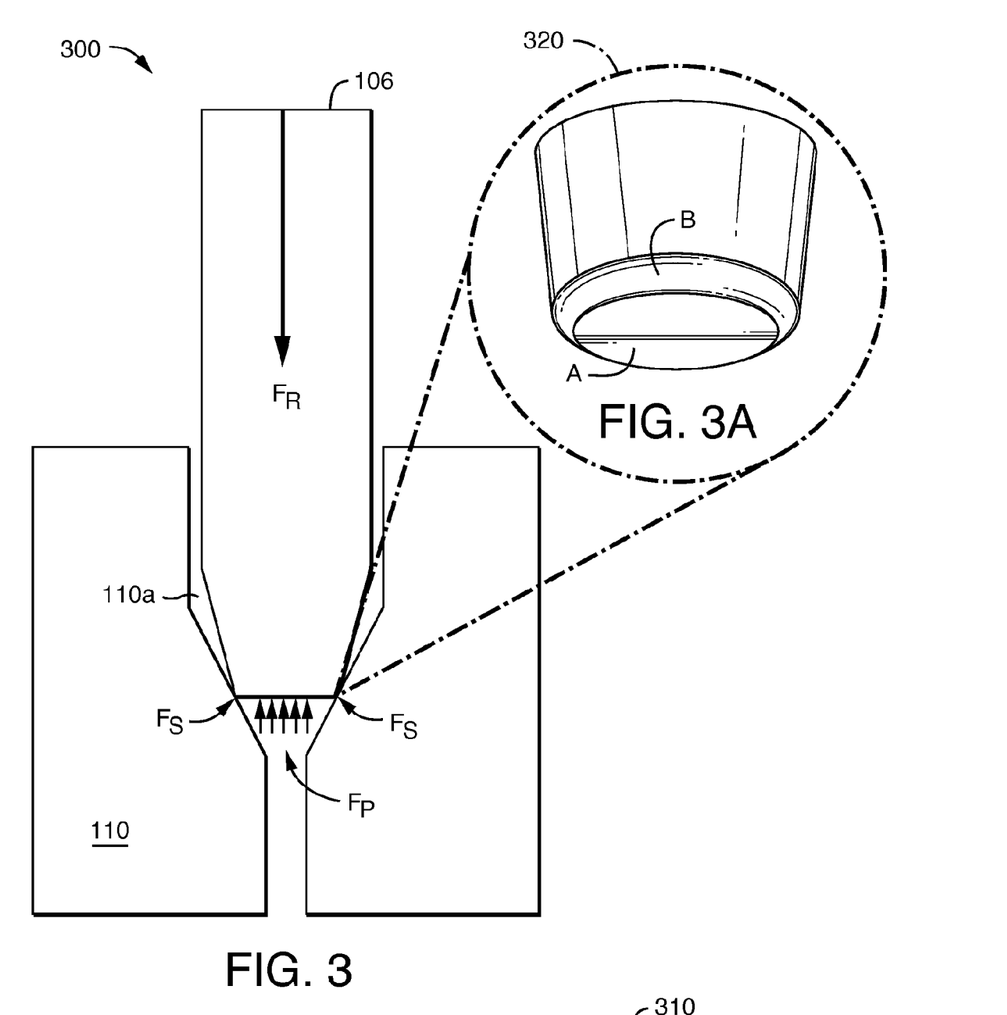
FIG. 3 is an example illustrating additional detail regarding a needle and needle seal and related forces in an embodiment in accordance with techniques described herein.
Figure 3B:
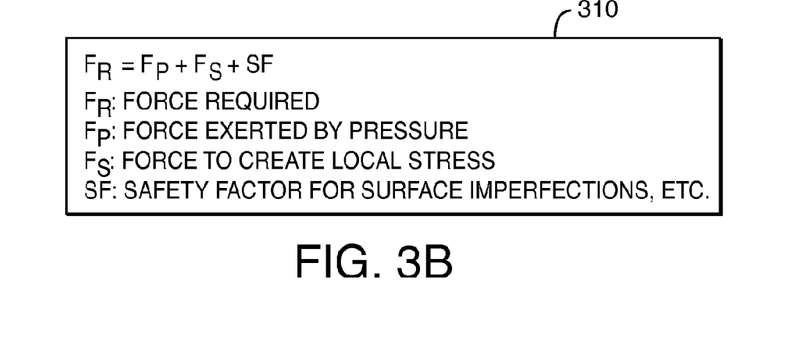

Referring to FIG. 3, shown is an example 300 of how Fr may be determined for use in accordance with techniques herein. The example 300 also provides an enlarged view of the needle seal 110 and needle 106 where surfaces of the tip of needle 106 and needle seal 110 come into contact and form the seal. Element 310 illustrates that Fr, a required force applied to the needle sufficient to form the seal between the surfaces of the needle tip and needle seal, may be represented as a sum of forces:

$$Fr=Fp+Fs+SF \qquad \text{EQUATION 2}$$

where
Fp is the force exerted by system pressure;
Fs is the force necessary to create local stress at the surfaces of the seal; and
SF is a safety factor or amount of force that may be added to account for any surface imperfections of the needle seal 110 and other possible conditions. SF may be determined in a variety of different ways such as based on knowledge and experience, as a percentage of one or more other calculations, and the like. Based on EQUATION 2, as one or more of Fs and Fp increase, so does Fr. As also known in the art, both stress (σ) and pressure (P) are proportional to an amount of force exerted over a given area. The foregoing may be represented as:

$$P=\text{FORCE/AREA} \qquad \text{EQUATION 3}$$

$$\text{STRESS=FORCE/AREA} \qquad \text{EQUATION 4}$$

Both Fp and Fs may be determined based on a mathematical calculation using the foregoing equations and the known operating system pressure P, such as 15,000 psi or 20,000 psi, at which the LC system may operate. For each of Fs and Fp, an estimation of area may be made. Element 320 illustrates one way in which an embodiment may estimate the areas for determining Fs and Fp for a given system pressure P. In calculating Fp for a given system pressure P, the area may be the sum of AREA A and AREA B. AREA A may be the surface area of the underside of the needle tip when the seal is formed and AREA B may be the surface area at the sides of the needle tip in contact with the surface of the needle seal. An embodiment may use AREA B as an estimate of the area when calculating Fs for a given system pressure P. The values for P (or stress) used in determining each of Fs and Fp are based on the system operating pressure (e.g., 20 kpsi) alone and/or in combination with other values. The other values may take into account any additional mechanical effects in a given system embodiment.

It should be noted that the foregoing is only one way in which Fr for a system may be determined. Fr for a particular system and application may be specified by a vendor, manufacturer, distributor, and the like. For example, in one embodiment of an LC system operating at 20,000 psi in accordance with force sensing techniques herein, Fr may be determined as 5.4 lbs or 5.5 lbs for an estimated stress or pressure of 64,000 psi based on Fp, Fs, and SF from EQUATION 2.

Figure 4:
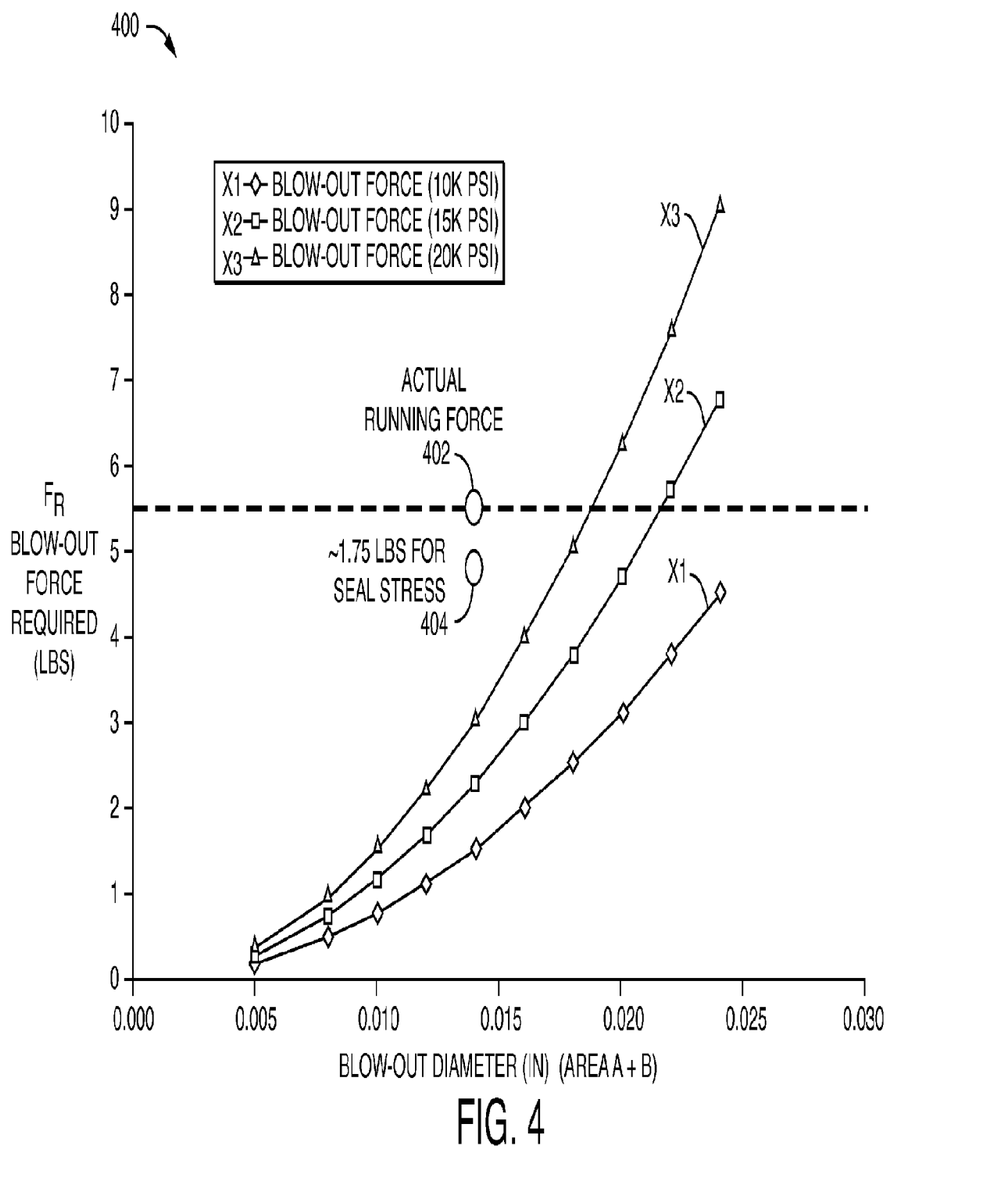
FIGS. 4 and 5 provide graphical illustrations related to forces in accordance with techniques herein.

Referring to FIG. 4, shown is a graphical illustration of Fr as may be used in an embodiment in accordance with techniques herein. The example 400 illustrates how Fr (Y axis values) may vary with diameter of the area represented as AREA A+AREA B (X axis values) described above in connection with FIG. 3. Curve X1 represents values for Fr (Y axis) for a given diameter (X-axis) with an operating system pressure of 10,000 psi. Curve X2 and Curve X3 similarly represent values for Fr with, respectively, operating system pressures of 15,000 psi and 20,000 psi. The line passing through 402 may represent the Fr=5.5 lbs as mentioned above. Element 404 may represent a theoretical calculation for Fr based on operating system pressure alone. Element 402 may represent the force required Fr based on the operating system pressure in combination with other factors of a given embodiment that may increase the force required along with any desired safety factor.

Figure 5A:
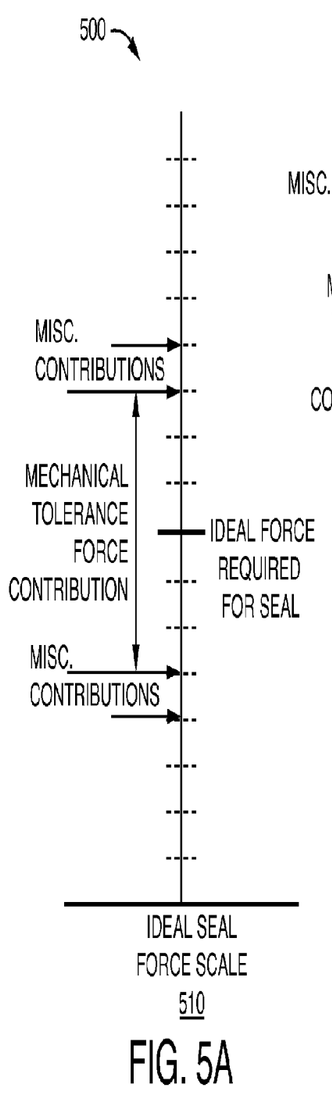
Figures 5B, 5C:
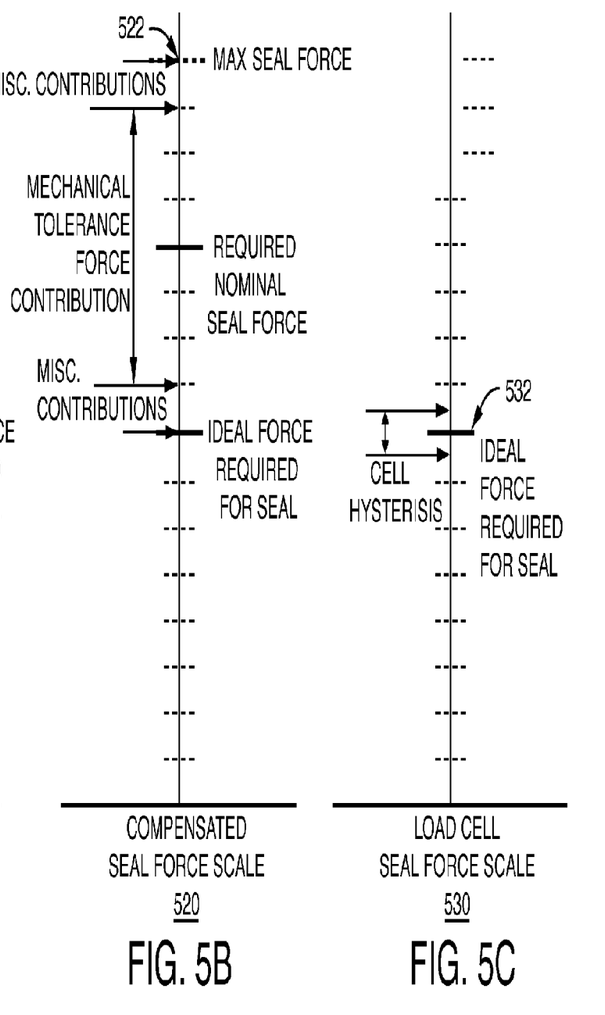

Referring to FIG. 5, shown are graphical illustrations of forces in systems with and without using the force sensing techniques described herein. Elements 510 and 520 provide exemplary illustrations of how a selected force may be determined for use in a system which does not use the force sensing techniques described herein with the load cell. In an exemplary LC system without using the force sensing techniques described herein, an amount of force applied to the needle in forming the seal as described above takes into account mechanical tolerances, calibration errors, and the like, that may exist in a system. Element 510 may represent such a sealing force scale when considering possible mechanical tolerances. Element 520 may represent the scale of 510 further modified to compensate for additional conditions that may exist in a system, such as calibration errors, as well as compliance tolerances, and the like. Thus, element 520 may represent worst case conditions that may be considered in a system when selecting an appropriate force. An embodiment without using the force sensing techniques herein may apply a force as represented by 522 to account for such worst case conditions and ensure a sufficient force is applied when forming the seal between the contacting surfaces of the needle tip and needle seal. As illustrated by 510 and 520, the selected force may be determined in accordance with EQUATION 2 using compensated values for Fs, Fp and SF to account for such worst case conditions. In such an embodiment without using the force sensing techniques herein, the system may be configured to use a fixed vertical position of the needle in accordance with such worst case conditions.

Element 530 illustrates a force scale in connection with an embodiment using the force sensing techniques herein such as the exemplary embodiment of FIG. 1. Element 532 represents the force that may be selected for use in a system herein in accordance with EQUATION 2 without requiring additional compensation for worst case conditions of mechanical tolerances, calibration errors, and the like, that may present in a system. In an embodiment using a load cell, the load cell may have an associated variance or error (e.g., based on load cell hysteresis) in connection with force readings obtained. As such, a force Fr as represented by 532 may be determined in accordance with EQUATION 2 where, for example, SF may take into account for possible variance or error of the load cell.

Figure 6:
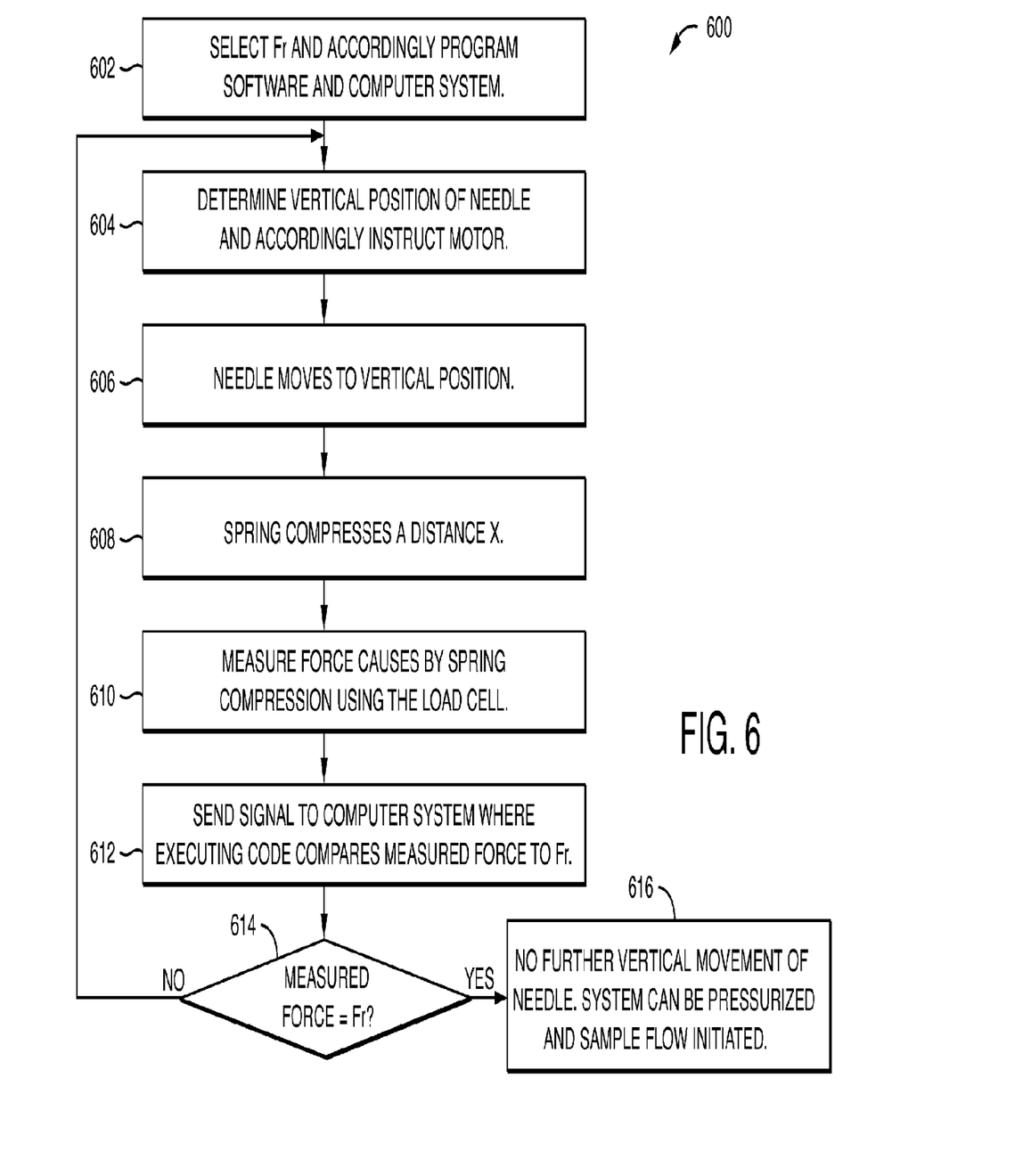
FIG. 6 is a flowchart of processing steps that may be performed in an embodiment in accordance with techniques described herein.

Referring to FIG. 6, shown is a flowchart of processing steps that may be performed in an embodiment in accordance with the techniques herein. The flowchart 600 summarizes processing as may be performed during operation of the embodiment of FIG. 1 described above when adjusting the vertical position of the needle in accordance with a selected Fr.

At step 602, Fr is selected and the software and computer system are accordingly programmed to use Fr as the desired force to achieve. At step 604, the code executing on the computer system may determine an initial vertical position for the needle and accordingly instruct the motor. The motor may cause the arm and needle to move vertically to the appropriate position in step 606 thereby causing the needle tip to contact a surface of the needle seal and the needle seal to move downward. At step 608, the downward movement of the needle seal due to the positioning of the needle causes compression of the spring a distance x. At step 610, the force caused by the spring compression is measured using the load cell. The amount of force measured is proportional to the amount of compression of the spring, x. At step 612, the load cell sends a signal to the computer system where the signal indicates the measured force. The code executing on the computer system compares the measured force to Fr and determines, at step 614, whether the measured force=Fr. If step 614 evaluates to yes, control proceeds to step 616 where there is no further vertical movement of the needle. The system can be pressurized and the sample flow initiated. If step 614 evaluates to no, control proceeds to step 604 where an adjusted vertical position is determined and processing is repeatedly performed to accordingly position the needle causing compression of the spring (steps 606, 608), measure the force caused by the spring compression (step 610), communicate the measured force to the computer system (612), and determine whether the measured force=Fr (step 614). As illustrated, steps 604, 606, 608, 610, 612, and 614 may be repeated until the vertical positioning of the needle causes sufficient force Fr to be applied to the needle seal as determined when the measured force=Fr. The steps of the flowchart 600 may be performed with respect to each volume of a sample which is aspirated into the needle prior to pressurizing the system causing injection of the sample.

It should be noted that when comparing a measured force to Fr (e.g., where Fr may be specified as a desired force setting programmed as described above), the measured force may be determined to be the same as Fr if both values are within a specified threshold amount of one another. The foregoing threshold may be determined empirically, based on knowledge by those skilled in the art, or using any suitable technique.

It should also be noted that in the exemplary embodiment described above, a single computing device is illustrated as performing processing steps described. However, an embodiment may use one or more computing devices in connection with performing processing as described herein.

Systems using direct injection without the techniques described herein for force sensing may be configured to consider worst case conditions (such as related to mechanical tolerances, calibration errors and the like) affecting an amount of force required to form the seal where the needle tip contacts the needle seal. Utilizing the force sensing techniques herein (e.g., such as with a load cell and a feedback loop), the amount of force applied to the needle in forming the seal may be reduced since the applied force does not have to account for the same set of worst case conditions. A reduction in the force applied to the needle and needle seal provides for reduced needle seal wear thus extending the needle seal lifetime.

With the force sensing techniques described herein, the system can automatically adjust the vertical needle position to achieve an Fr where the Fr is programmed as the desired force to achieve such as using the computer system and software described above. For example, at a first point in time, a UPLC system in accordance with techniques herein may operate at 20,000 psi and the system may be programmed to achieve a first Fr. At a later point in time, the operating system pressure may be reduced, for example, to 15,000 or 10,000 psi and an updated second Fr may be accordingly selected. As described herein, the second Fr will be less that the first Fr. Using the techniques herein, the system may be programmed to use the updated second Fr (e.g., programming using the software and computer system) and the system will automatically adjust the vertical needle position so that there is a reduction in the distance or amount of spring compression and less force is applied to the needle and needle tip. An embodiment using the force sensing techniques described herein does not require manual recalibration of vertical needle positioning since this adjustment may be automatically performed by reprogramming the desired Fr. For example, with reference to FIG. 1, the code executing on the computer system 18 may specify Fr as a programmable parameter which can be modified (such as when the operating system pressure changes) and accordingly causes the system to be tuned in accordance with an updated Fr. Thus, the needle seal life may be extended when operating at lower system pressures without requiring complicated recalibrations.

An embodiment of a system using the force sensing techniques herein may also provide other advantages and uses. The force sensing techniques herein may be used for performing system diagnostics. For example, the force sensing techniques may be used to detect a bad or worn needle seal. If a proper force reading is obtained using the force sensing techniques and a seal is not forming, a determination may be made that the needle seal should be replaced. As another example, the force sensing techniques may be used to detect other system problems. If a desired or programmed force cannot be reached (e.g., the reading obtained by the load cell is always lower than the programmed Fr), there may be problem with the motor, arm, and/or other component(s) used in vertically positioning the needle. The foregoing problem may be determine, for example, if a maximum downward vertical position of said needle does not cause a force measured by the force sensor to be at least equal to the desired force setting.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. An apparatus comprising:
    a needle positioned at a vertical position determined in accordance with a desired force setting;
    a positioning device configured to position said needle at said vertical position in response to control signals;
    a sealing member having a passage with a first opening at a first end for receiving one end of said needle, wherein positioning said needle at said vertical position causes application of a force, to an end face of said one end of said needle, downward in a vertical direction to form a substantially fluid tight seal between surfaces of said sealing member in contact with surfaces of said end face of said one end of said needle, said end face facing said vertical direction in which said force is applied, wherein when positioning the needle, once the surfaces of the end face of the needle are in contact with the surfaces of the sealing member, further downward vertical movement to position the needle results in the sealing member being pushed vertically downward thereby causing compression of a spring towards a force sensor;
    the spring which, responsive to application of said force, is compressed a distance vertically whereby the distance is proportional to said force applied downward in the vertical direction;
    the force sensor coupled to the spring, said force sensor measuring said force; and
    a computing device electrically connected to said force sensor and said positioning device, said computing device configured to receive a signal from said force sensor indicating said force measured by the force sensor.

2. The apparatus of claim 1, wherein said computing device is further configured to determine an adjustment to said vertical position of said needle in accordance with whether said force measured by said force sensor is at said desired force setting, and configured to send control signals to said positioning device causing said positioning device to vertically position said needle in accordance with said adjustment.

3. The apparatus of claim 1, wherein said computing device includes a computer processor.

4. The apparatus of claim 2, further including a non-transitory computer readable medium comprising executable code stored thereon that:
    determines an adjustment to said vertical position of said needle in accordance with whether said force being applied is at said desired force setting; and
    sends control signals to said positioning device causing said positioning device to vertically position said needle in accordance with an adjustment determined by said code that determines an adjustment.

5. The apparatus of claim 1, wherein said positioning device includes a motor which incrementally adjusts vertical positioning of said needle responsive to control signals from said computing device.

6. The apparatus of claim 2, wherein said desired force setting is an amount of force determined as sufficient to create said substantially fluid tight seal at said surfaces of said sealing member which are in contact with said surfaces of the end face of the one end of said needle when a system including said apparatus is pressurized.

7. The apparatus of claim 1, wherein said apparatus is included in a system that performs liquid chromatography.

8. The apparatus of claim 1, wherein said apparatus is included in a component that performs direct injection of a sample aspirated into said needle.

9. The apparatus of claim 1, wherein the sealing member is a needle seal and said first opening at said first end thereof is inwardly tapered and sidewalls of said first opening are in contact with said surfaces of said end face of said one end of said needle.

10. The apparatus of claim 4, wherein the non-transitory computer readable medium further includes executable code stored thereon that:
    compares said force measured by said force sensor to said desired force setting to determine whether to make any adjustment to said vertical position of said needle.

11. The apparatus of claim 10, wherein the non-transitory computer readable medium further includes executable code stored thereon that:
    determines, if said force measured is less than said desired force setting, an adjustment which, when applied to the needle, causes said needle to be further adjusted vertically downward causing said spring to compress another amount in addition to said distance.

12. The apparatus of claim 10, wherein the non-transitory computer readable medium further include executable code stored thereon that:
determines, if said force measured is more than said desired force setting, an adjustment which, when applied to the needle, causes said needle to be further adjusted vertically upward causing said spring to compress a lesser amount than said distance.

13. The apparatus of claim 2, wherein said desired force setting varies in accordance with an operating pressure of a system including said apparatus.

14. The apparatus of claim 1, wherein said force sensor includes a load cell.

15. A method for force sensing comprising:
configuring a computing device to have a desired force setting;
determining, using said computing device in accordance with a desired force setting, a first vertical position of a needle;
sending a control signal from said computing device to a positioning device;
positioning, in response to said control signal and using said positioning device, said needle at said first vertical position, wherein when in said first vertical position, surfaces of an end face of one end of said needle are in contact with surfaces of sidewalls in an opening of a sealing member and said positioning causes application of a force, to said end face of said one end of the needle, downward in a vertical direction to form a substantially fluid tight seal between surfaces of said sidewalls of the opening in contact with surfaces of said end face of the one end of said needle, wherein said end face of said one end of said needle faces said vertical direction in which the force is applied;
compressing, responsive to application of said force, a spring a distance vertically that is proportional to said force applied in the vertical direction; and
measuring said force using a force sensor, wherein when positioning the needle, once the surfaces of the end face of the needle are in contact with the surfaces of the sidewalls in the opening of the sealing member, further downward vertical movement to position the needle results in the sealing member being pushed vertically downward thereby causing compression of the spring towards the force sensor.

16. The method of claim 15, further comprising:
determining, using said computing device, whether to adjust said first vertical position of said needle in accordance with whether said force measured using said force sensor is at said desired force setting.

17. The method of claim 16, wherein said computing device includes a computer processor which executes code stored in a memory to perform processing, said processing including said determining a first vertical position, said sending, and said determining whether to adjust said first vertical position.

18. The method of claim 16, further comprising:
receiving, by said computing device, a signal from said force sensor, said signal indicating said force measured by said force sensor;
comparing, using said computing device, said force measured by said force sensor to said desired force setting; and
determining, using said computing device, a vertical positioning adjustment in accordance with said comparing.

19. The method of claim 18, wherein if said measured force is less than said desired force setting, the method further comprising:
determining said vertical positioning adjustment which, when applied to the needle, causes said first vertical position of said needle to be further adjusted vertically downward causing said spring to compress another amount in addition to said distance.

20. The method of claim 18, wherein if said force measured is more than said desired force setting, the method further comprising:
determining, said vertical positioning adjustment which, when applied to the needle, causes said first vertical position of said needle to be further adjusted vertically upward causing said spring to compress a lesser amount than said distance.

21. The method of claim 16, wherein said desired force setting is an amount of force determined as sufficient to create said substantially fluid tight seal at said surfaces of said sidewalls of said sealing member which are in contact with surfaces of said surfaces of the end face of the one end of said needle when a system in which said method is being performed is pressurized.

22. The method of claim 15, wherein said force is a sealing force applied in a system that performs liquid chromatography.

23. The method of claim 16, wherein vertical positioning of said needle is readjusted until said measured force equals said desired force setting determined as sufficient to form said substantially fluid tight seal at said surfaces of said sidewalls of said sealing member which are in contact with said surfaces of the end face of said one end of said needle when a system in which said method is being performed is pressurized.

24. The method of claim 15, further comprising aspirating a sample into said needle prior to positioning said needle at said first vertical position.

25. The method of claim 16, wherein said desired force setting varies in accordance with an operating pressure of a system in which said method is performed.

26. The method of claim 15, wherein said force sensor includes a load cell.

27. The method of claim 15, wherein said sealing member is a needle seal.

28. The method of claim 16, further comprising:
determining that said sealing member should be replaced if the force measured by the force sensor is at least the desired force setting and said substantially fluid tight seal is not formed when a system is pressurized.

29. The method of claim 16, further comprising:
determining a problem with a component of said positioning device if a maximum downward vertical position of said needle does not cause a force measured by the force sensor to be at least equal to the desired force setting.

* * * * *